United States Patent [19]

Singleton

[11] 4,132,734

[45] Jan. 2, 1979

[54] SYNTHESIS OF CARBOXYLIC ACIDS

[75] Inventor: Thomas C. Singleton, Texas City, Tex.

[73] Assignee: Monsanto Company, St. Louis, Mo.

[21] Appl. No.: 682,232

[22] Filed: May 3, 1976

[51] Int. Cl.$^2$ ............................................. C07C 51/14
[52] U.S. Cl. ................................ 562/522; 260/326.2; 260/327 R; 260/347.3; 260/397.1; 260/413; 260/465.4; 562/406; 562/497
[58] Field of Search ........... 260/533 AN, 514 M, 413, 260/515 R, 532, 526 R

[56]  References Cited
U.S. PATENT DOCUMENTS

| Re. 27,360 | 5/1972  | Olivier .............................. 260/497 A |
| 3,579,551  | 5/1971  | Craddock et al. ................... 260/413    |
| 3,579,552  | 5/1971  | Craddock et al. ................... 260/413    |
| 3,661,949  | 5/1972  | Fenton ............................. 260/533 AN |
| 3,717,670  | 2/1973  | Schultz ........................... 260/533 AN  |
| 3,769,329  | 10/1973 | Paulik et al. ..................... 260/532     |
| 3,772,380  | 10/1973 | Paulik et al. ..................... 260/532     |

*Primary Examiner*—Vivian Garner
*Attorney, Agent, or Firm*—James C. Bolding; Elizabeth F. Sporar

[57]  ABSTRACT

The rate of reaction of ethylenically unsaturated compounds, carbon monoxide and water in the presence of catalyst systems consisting essentially of a rhodium or iridium compound and a halogen promoter to produce carboxylic acids is accelerated by including a minor amount of a compound of cobalt, iron or manganese in the reaction system.

7 Claims, No Drawings

SYNTHESIS OF CARBOXYLIC ACIDS

BACKGROUND OF THE INVENTION

The present invention relates to an improvement in the process for the preparation of carboxylic acids prepared by the reaction of ethylenically unsaturated compounds with carbon monoxide and water in the presence of catalyst compositions comprising rhodium or iridium compounnds and a halogen promoter. More particularly, the invention relates to increasing the rate of reaction in such a process by employing certain compounds as additives in the reaction.

The preparation of carboxylic acids and ester derivatives thereof from olefins and other ethylenically unsaturated compounds, carbon monoxide and water is well known in the art. A number of catalysts have been disclosed for the reaction at elevated temperatures and pressures. More recently, a process has been developed which employs more reactive and more stable catalysts whereby lower temperatures and pressures can be employed in the process resulting in a higher yield of the desired carboxylic acid with no substantial formation of undesirable by-products. These catalysts generally contain two components, namely, a rhodium or iridum compound and a halogen component. The catalysts and the process in which they are employed are described in detail in U.S. Pat. Nos. 3,579,552 and 3,579,551. While this process is, in general, satisfactory for commercial operation, it has now been discovered that production of acid per unit time can be substantially increased by carrying out the reaction in the presence of certain compounds which accelerate the rate of reaction, hereinafter referred to simply as "accelerators."

SUMMARY OF THE INVENTION

In accordance with the present invention, ethylenically unsaturated compounds are converted selectively to carboxylic acids by reaction with carbon monoxide and water at temperatures from about 50° C. to about 300° C. and at partial pressures of carbon monoxide from about 1 psia to 15,000 psia in contact with a catalyst system consisting essentially of a rhodium or iridium compound and a halogen component and as an accelerator for the reaction a compound of a metal selected from the group consisting of cobalt, iron and manganese. In the preferred embodiment of the invention, propionic acid is produced by the reaction of ethylene, carbon monoxide and water at temperatures from about 125° C. to about 225° C. and at partial pressures of carbon monoxide from about 5 psia to about 3000 psia in contact with a catalyst system consisting essentially of a rhodium compound and an iodide as the halogen component and as an accelerator for the reaction, a compound of cobalt, iron or manganese.

DESCRIPTION OF THE PREFERRED EMBODIMENTS

The ethylenically unsaturated compounds which may be reacted to produce monocarboxylic acids according to the present invention include those having from 2 to 30 carbon atoms and containing the structural unit

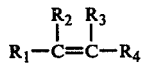

in aliphatic, cyclic, polycyclic, heteroaliphatic or heterocyclic form in which $R_1$, $R_2$, $R_3$ and $R_4$ are moieties having 0 to 20 carbon atoms and are selected from the group consisting of hydrogen, halogen, alkyl, alkenyl, aryl, cycloalkyl and cycloalkenyl moieties, said hetero compounds being substituted with nitrogen, phosphorus, sulfur or oxygen atoms. Representative of such compounds are ethylene, propylene, butenes, hexenes, octenes, hexadecene, 2-methylpropene; 1,3-butadiene, 2-methyl-1,3-butadiene; 2,3-dimethyl-1,3-butadiene; cyclohexene; methyl-cyclohexene; styrene; methylstyrene; vinylcyclohexene; 3,3-dimethyl-1-butene; 1,4-hexadiene; 2,4-hexadiene; 1,5-hexadiene; 2-methyl-1,4-hexadiene; acrolein; methyl vinyl ketone; allyl alcohol; 2-phenylbutene; cyclopentadiene; 2-cyclohexylbutene; allene; allylamine; diallylamine; acrylonitrile; vinyl chloride; phosphopyruvic acid; and mixtures thereof. Other suitable feedstocks include compounds having cyclic and polycyclic structures containing, in part, an ethylenically unsaturated linkage which may be converted to a carboxylic acid by the process of this invention. Examples of suitable cyclic structures include 1,5-cyclooctadiene; 1,5,9-cyclododecatriene; furan; 1,2-dithiol; pyrrole and cholesterol; α-terpineol, β-amgrin, progesterone, abietic acid, limonene and α-pinene.

A typical carbonylation reaction selective to a carboxylic acid requires stoichiometric quantities of the reactants, that is at least one mole of carbon monoxide and one mole of water per mole (equivalent) of ethylenically unsaturated linkage reacted. An amount of carbon monoxide and water, however, in excess of the stoichiometric quantity may be employed.

Carbon monoxide streams containing part impurities such as carbon dioxide, methane, nitrogen, noble gases and paraffinic hydrocarbons having from 1 to 4 carbon atoms such as are available in plant gas streams may be employed if desired. In such cases, however, total reactor pressure will have to be increased to maintain a desired carbon monoxide pressure. The concentration of carbon monoxide in the feed gas can be from 1 volume percent to 99.9 volume percent, the preferred range being from about 10 volume percent to 99.9 volume percent.

The ethylenically unsaturated feedstock is normally charged with equimolar amounts of water, i.e., at least a molar quantity of water is present equivalent to the number of moles of ethylenically unsaturated linkage reacted, although more water may be used.

The reaction is conducted at temperatures in the range from about 50° C. to about 300° C. and preferably from about 125° C. to about 225° C. Partial pressures of carbon monoxide of the order of 1 psia to 15,000 psia may be employed; however, pressures from 5 psia to 3000 psia are preferred and partial pressures from 25 psia to 1000 psia are even more preferred.

The catalyst systems used for the process of the invention are described in U.S. Pat. Nos. 3,579,552 and 3,579,551, the detailed disclosures of which are incorporated herein by reference. In general, such systems consist essentially of a rhodium or iridium compound and a halogen component. The active catalytic portion is the rhodium or iridium compound such as the salts, oxides, organometal compounds and coordination compounds of these metals. In the preferred catalyst systems, the salts, oxides and carbonyls of these metals consisting only of the metal and carbonyl moieties are employed. The halogen component of the catalyst system is supplied as the free halogen, e.g., bromine or iodine, or as a halogen compound such as hydrogen halide, alkyl or aryl halide, metal halide, ammonium, phosphonium, arsonium, stibonium halide etc., wherein the halogen is either bromine or iodine. Iodine or iodide compounds are preferred for use as the halogen component of the catalyst system with hydrogen iodide or an alkyl iodide constituting the more preferred species. The halogen component may be charged to the reactor separately from the active metal compound or it may be incorporated into the active metal compound, e.g., $RhI_3$, $RhI[C_6H_5P]_3$, $Ir(CO)_2Br_2$, etc. Generally, however, it is preferred that the catalyst system contain as the halogen component an excess of halogen over that present as ligands in the rhodium or iridium complex. Ratios of halogen component to metal compound expressed as atoms of halogen to atoms of rhodium or iridium are in the range from 1:1 to 2500:1 but the preferred range is from 3 to 300 halogen atoms per rhodium or iridium atom.

The catalyst system may be preformed prior to charging to the reactor or it may be formed in situ in the reactor. The metal compound is preferably supplied as a catalyst solution which can also include liquid reactants, products and mixtures thereof which function as solvents or reaction media.

Concentrations of the rhodium or iridium compound of the catalyst system in the liquid phase between $10^{-6}$ mole/liter and $10^{-1}$ mole/liter are normally employed, with the preferred range being $10^{-4}$ mole/liter to $10^{-2}$. Higher concentrations even to the extent of 1 mole/liter may, however, be used if desired. Higher temperatures also favor higher reaction rates.

The concentration of the halogen component of the catalyst system may vary widely over the broad concentration range of $10^{-6}$ mole/liter to 18 moles/liter, based on halogen atom. In the process of this invention, however, the preferred concentration range of halogen component is $10^{-4}$ mole/liter to 2 moles/liter of catalyst solution.

The reaction may be conducted in either the liquid or vapor-phase. In the vapor-phase operation, the metal-containing catalyst system is dispersed on an inert support and employed in a conventional fixed-bed catalytic reactor maintained at the temperature and pressure conditions described above wherein the reactants are passed over the catalyst. Suitable support materials include, for example, alundum, activated carbon, clays, alumina, alumina silica, ceramics, etc. Preferably, however, the reaction is carried out in the liquid phase using as a liquid reaction medium any solvent compatible with the catalyst system such as pure olefins, mixtures of an olefin feedstock and/or the desired carboxylic acid and/or other carboxylic acids such as acetic acid. The preferred solvent and liquid reaction medium for the process of the invention is a monocarboxylic acid having 2–20 carbon atoms, e.g., acetic, propionic, nonanoic, naphthoic and elaidic acids including isomeric forms. Water may also be added to the reaction mixture.

The accelerators which provide the improvement of the present invention are compounds of cobalt, iron and manganese such as the salts, oxides, hydroxides and acetates of these metals. The latter compounds are usually employed with an equivalent amount of hydrogen iodide, i.e., two parts HI per part of acetate. Suitable metal compounds include, for example, ferrous and ferric chlorides, ferrous and ferric bromides, ferrous and ferric iodides, ferrous and ferric oxides, ferrous and ferric hydroxides, cobaltous and cobaltic bromides, cobaltous and cobaltic iodides, manganous and manganic iodides, manganous and manganic bromides, manganous and manganic acetates, cobaltous and cobaltic oxides, and the like.

Only minor amounts of the accelerator are required. Depending upon the initial concentration of water in the reaction mixture, the concentration of accelerator may range from as low as 0.001 molar to an upper limit which is determined only by the solubility of the accelerator in the reaction medium. Preferably, however, a molar concentration in the reaction from about 0.005 to 0.1 is maintained. The accelerators are always effective in reactions wherein the molar concentration of water is less than 6. At water concentrations greater than 6 molar, the same metal compounds may accelerate or retard the reaction depending upon iodine concentration.

The accelerator may be introduced into the reaction in any convenient manner. It may be added separately to the reactor, with any of the feed materials, or it may be introduced in the catalyst solution or reaction medium. Preferably, it is added with the catalyst solution.

The invention is illustrated in the following example which, however, is not to be construed as limiting it in any manner whatsoever.

EXAMPLE

A one-liter Hastelloy-B autoclave equipped with a mechanical agitator serving as a reactor was flushed with carbon monoxide (CO). The reactor was charged with a solution of rhodium carbonyl iodide complex, water, ethyl iodide and propionic acid employed as a reaction medium and when used, a minor amount of a compound of a metal selected from the group consisting of cobalt, iron and manganese dissolved in propionic acid. Initial liquid volume was about 400 ml with a rhodium concentration of 0.0005 molar and a total iodine concentration of 0.5 molar. The autoclave was blocked in and a sufficient amount of CO (0.18 mole) was charged to provide a partial pressure of this reactant of about 100 psi at reaction conditions. The autoclave was heated with stirring (1215 rpm) to a reaction temperature of 185° C. and sufficient ethylene was then admitted to provide a partial pressure of this reactant at reaction conditions of 200 psi. A 1:1 molar mixture of CO and ethylene was then fed into the reactor from a gas reservoir to maintain constant pressure in the reactor. Rate of reaction was determined from the rate of pressure drop in the CO-ethylene feed gas reservoir, the reservoir volume and predetermined pressure-mole factors for the feed gases. Calculated results presented in the table below clearly demonstrate the increase in reaction rate effected by the inclusion of the metal compound in the reaction.

| Run | Initial $H_2O$ Conc. (Moles/l) | Calculated $H_2O$ During Rate Calc. (Moles/l) | Metal Additive | Metal Additive Conc. (Moles/l) | Rate Moles/l/hr |
|---|---|---|---|---|---|
| 1 | 1.7 | 1.2–0.8 | None | — | 6.6 |
| 2 | " | " | $FeI_2$ | 0.01 | 9.9 |
| 3 | 3.7 | 3.2–2.7 | None | — | 4.0 |
| 4 | " | " | $FeI_2$ | 0.01 | 6.0 |
| 5 | " | " | $CoI_2$ | 0.01 | 7.2 |
| 6 | " | " | $MnI_2$ | 0.01 | 6.0 |
| 7 | 5.7 | 5.2–4.7 | None | — | 4.4 |
| 8 | " | 5.1–4.5 | $FeI_2$ | 0.01 | 5.1 |
| 9 | " | 5.1–4.6 | $CoI_2$ | 0.01 | 6.2 |

What is claimed is:

1. In the process of converting to a carboxylic acid an ethylenically unsaturated compound having 2 to 30 carbon atoms having the structural formula

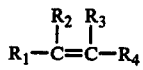

in which $R_1$, $R_2$, $R_3$ and $R_4$ are moieties having 0 to 20 carbon atoms and are selected from the group consisting of hydrogen and alkyl moieties by reacting in a liquid medium said compound, carbon monoxide and water in contact with a catalyst system consisting essentially of a rhodium or iridium oxide, salt, or carbonyl consisting only of the metal and carbonyl moieties, and a halogen component selected from the group consisting of bromine, iodine, alkyl bromide, alkyl iodide, hydrogen iodide, and hydrogen bromide at a temperature from about 50° to about 300° C. and a carbon monoxide partial pressure in the range from about 1 to about 15,000 psia, the improvement which comprises including in said reaction as an accelerator therefor a metal compound selected from the group consisting of the salts, oxides and hydroxides of cobalt, iron and manganese, the concentration of said metal compound being in the range from about 0.005 to about 0.1 molar and maintaining said water concentration at less than 6 molar.

2. The process of claim 1 wherein said ethylenically unsaturated compound is ethylene.

3. The process of claim 2 wherein said liquid reaction medium is propionic acid.

4. The process of claim 3 wherein said catalyst system consists essentially of a rhodium compound and an iodide.

5. The process of claim 4 wherein said metal compound accelerator is a compound of cobalt.

6. The process of claim 4 wherein said metal compound accelerator is a compound of iron.

7. The process of claim 4 wherein said metal compound accelerator is a compound of manganese.